United States Patent
Sathish et al.

(10) Patent No.: US 7,716,987 B2
(45) Date of Patent: May 18, 2010

(54) NON-CONTACT THERMO-ELASTIC PROPERTY MEASUREMENT AND IMAGING SYSTEM FOR QUANTITATIVE NONDESTRUCTIVE EVALUATION OF MATERIALS

(75) Inventors: Shamachary Sathish, Bellbrook, OH (US); Richard Reibel, Dayton, OH (US); John T. Welter, Fairborn, OH (US); Charles Buynak, Tipp City, OH (US)

(73) Assignee: University of Dayton, Dayton, OH (US)

( * ) Notice: Subject to any disclaimer, the term of this patent is extended or adjusted under 35 U.S.C. 154(b) by 16 days.

(21) Appl. No.: 11/496,116

(22) Filed: Jul. 31, 2006

(65) Prior Publication Data

US 2008/0022775 A1    Jan. 31, 2008

(51) Int. Cl.
*G01N 29/04* (2006.01)
*G01N 25/00* (2006.01)
*G01J 5/02* (2006.01)

(52) U.S. Cl. .................. 73/589; 73/606; 250/341.1; 250/341.6; 374/45

(58) Field of Classification Search .................. 73/579, 73/589, 601, 606; 250/341.1, 341.6, 358.1, 250/330, 334; 258/342; 374/45, 121
See application file for complete search history.

(56) References Cited

U.S. PATENT DOCUMENTS

| | | | |
|---|---|---|---|
| 4,513,384 A | 4/1985 | Rosencwaig | |
| 4,578,584 A | 3/1986 | Baumann et al. | |
| 5,124,640 A | 6/1992 | Chern | |
| 5,760,904 A | 6/1998 | Lorraine et al. | |
| 5,801,312 A | 9/1998 | Lorraine et al. | |
| 6,182,512 B1 | 2/2001 | Lorraine | |
| 6,236,049 B1 | 5/2001 | Thomas et al. | |

(Continued)

FOREIGN PATENT DOCUMENTS

EP    0 097 473 A1    4/1984

(Continued)

OTHER PUBLICATIONS

Rantala et al., NDT of polymer materials using lock-in thermography with water-coupled ultrasonic excitation; NDT&E International, 1998, vol. 31, No. 1, pp. 43-49, Great Britain.

(Continued)

*Primary Examiner*—Helen C. Kwok
(74) *Attorney, Agent, or Firm*—Dinsmore & Shohl LLP

(57) ABSTRACT

A non-contact thermo-elastic property measurement and imaging system and method thereof are described. Acoustic energy is incident on a first surface of a specimen under test. The acoustic energy is converted partially into heat by the specimen, causing a slight increase in the temperature in a region of interaction. The temperature increase is imaged using a high sensitivity infrared camera. Presence of defects (surface and subsurface) in the material modifies the distribution of temperature. An image of temperature distribution can be used for nondestructive testing and evaluation of materials. The temperature change in the specimen caused by acoustic excitation is related to thermal and elastic properties of the material. A measurement of the change in the temperature as a function of the amplitude of incident excitation can be used for direct measurement of thermo-elastic property of the specimen.

16 Claims, 4 Drawing Sheets

U.S. PATENT DOCUMENTS

| | | | |
|---|---|---|---|
| 6,399,948 | B1 | 6/2002 | Thomas et al. |
| 6,437,334 | B1 | 8/2002 | Thomas et al. |
| 6,593,574 | B2 | 7/2003 | Thomas et al. |
| 6,684,681 | B1 * | 2/2004 | Zombo ............... 73/12.11 |
| 6,759,659 | B2 | 7/2004 | Thomas et al. |
| 6,786,098 | B2 * | 9/2004 | Bates ................. 73/606 |
| 6,838,670 | B2 * | 1/2005 | Lewis et al. ........... 250/341.6 |
| 6,877,894 | B2 * | 4/2005 | Vona et al. ............. 374/45 |
| 6,998,616 | B2 * | 2/2006 | Favro et al. ........... 250/341.6 |
| 7,057,176 | B2 * | 6/2006 | Rothenfusser et al. ... 250/341.6 |
| 7,060,971 | B2 * | 6/2006 | Zombo et al. ........... 250/252.1 |
| 7,064,331 | B2 * | 6/2006 | Rothenfusser et al. ... 250/341.6 |
| 7,075,084 | B2 * | 7/2006 | Thompson et al. ....... 250/341.6 |
| 7,122,801 | B2 * | 10/2006 | Favro et al. ........... 250/341.6 |
| 7,131,331 | B2 * | 11/2006 | Bates ................. 73/589 |
| 7,199,367 | B2 * | 4/2007 | Favro et al. ........... 250/341.6 |
| 7,271,706 | B2 * | 9/2007 | Lee ................... 340/384.2 |
| 2002/0018510 | A1 | 2/2002 | Murphy et al. |
| 2006/0114965 | A1 | 6/2006 | Murphy et al. |

FOREIGN PATENT DOCUMENTS

WO    WO 2004/020993    *    3/2004

OTHER PUBLICATIONS

E. G. Henneke, II, et al.; Vibrothermography, Nondestructive Testing Handbook Special Nondestructive Testing Methods, 1995, Am. Soc. NDT, vol. 9, pp. 336-340, United States.

R. B. Mignogna, et al.; Thermographic investigation of high-power ultrasonic heating in materials; Jul. 1981, Ultrasonics, pp. 159-165.

* cited by examiner

NON-CONTACT THERMO-ELASTIC PROPERTY MEASUREMENT AND IMAGING SYSTEM FOR QUANTITATIVE NONDESTRUCTIVE EVALUATION OF MATERIALS

STATEMENT OF GOVERNMENT INTEREST

The invention described herein may be manufactured and used by and for the Government of the United States of America for Governmental purposes without the payment of any royalties thereon or thereto.

FIELD OF THE INVENTION

This invention relates generally to a system and method for the detection of defects in a material and, more particularly, to a non-contact thermo-elastic property measurement and imaging system for quantitative nondestructive evaluation of materials.

BACKGROUND OF THE INVENTION

Varieties of organic composites are in use for their superior strength and low density compared to metallic structures. These organic composites consist of fibers embedded in polymer matrices. Many layers are superposed on each other to obtain high strength and superior properties. For several decades, the aerospace industries have taken the advantage of superior physical properties and weight of the composite materials. Generally, composites of carbon fibers with polymer matrix are used in aerospace applications. While the polymer composites provide excellent strength/weight ratio, their strength degrades dramatically when exposed to heat. On an aircraft, this could happen due to fire accidents or accidental exposure to excessive heat during repair or due to heat generation due to lightening strike.

Several experimental techniques have been used to evaluate the heat damage in composites. Some of these techniques are nondestructive in nature and some are destructive. While destructive techniques essentially attempt to measure the loss of mechanical strength in the composite, nondestructive evaluation (NDE) techniques attempt to relate the measured property to the loss of strength. In particular, NDE techniques provide information about the elastic modulus of the degraded material. However, significant change in the elastic modulus occurs only when gross damage occurs in the material. Accordingly, prior art NDE techniques are not sensitive to detecting "incipient" damage in composites which is responsible for the loss of physical or mechanical properties without gross changes in structure such as cracking, blistering or delamination.

For example, NDE of materials based on acoustic wave propagation depends on the interaction of acoustic waves with defects in the material. In particular, prior art acoustic based NDE methods use the returned acoustic energy to measure elastic properties of materials and to identify defect locations in the material based on the changes in the elastic properties caused by presence of the defects. In such prior art acoustic wave propagation systems, for the best NDE testing results, a piezoelectric transducer is either placed in contact with the material or both the transducer and material to be tested are immersed in water in order to launch sufficient acoustic wave energy into the material.

Another non-contact NDE method is infrared (IR) thermography. IR thermography is used to detect and image changes in the thermal property of materials. In this prior art method, a heat pulse is incident on the surface of the material to be tested. The heat diffuses into the material uniformly causing gradual temperature changes. An IR camera is used to image the changes in the temperature. IR images are acquired as a function of time from the initial excitation of the heat pulse. Presence of defects in the material alters the distribution of temperature. Analysis of the IR images can be used to detect and locate the defects in the material. However, it has been observed that significant changes in thermal properties occur only when the composite has undergone gross damage. Changes in thermal properties during early stages of heat damage in composites are quite small and hence the IR thermography is not a sensitive method.

Another NDE technique is the thermo-elastic measurements. This technique takes the advantage of the slight reduction of temperature of the material, when subjected to tension, while a small increase in temperature is observed when subjected to compressive stress. The thermo-elastic technique is used in evaluation of the stress distribution under load in materials and components. The temperature distribution is most often measured using a high sensitivity infrared camera. Following similar arguments and instead of using mechanical loading to create a distribution of temperature, high amplitude acoustic wave can be used. The temperature distribution can be visualized using IR camera.

Another NDE technique combines acoustic excitation and IR thermography to evaluate the heat damage in composite materials. In this technique, an ultrasonic horn is brought into contact with the composite and the structure is excited. The high amplitude vibration caused by the horn, create vibrations of different modes in the specimen. In the neighborhood of a defect (crack or delamination), the modes of vibration create extra heat due to friction between the two faces of the crack or other irreversible thermo-elastic effects. Temperature changes due to vibrations are captured using a high sensitivity IR camera. However, this contact technique of exciting the structure with high amplitude ultrasonic waves raises concerns about the damage that could be introduced due to excitation process via direct contact between the composite and the acoustic horn. The acoustic horn in contact when excited operates like a hammer and may cause damage to the specimen. In addition, the relation between the temperature changes and the amount of heat damage is complicated by excitation of many different modes of vibration in the structure due to direct contact between the horn and specimen. This methodology is known in the literature by different names as, vibro-thermography, thermo-sonics, sonic-IR, etc.

Accordingly, it is to be appreciated that while many NDE techniques have been used in the past for evaluation of heat damage in composites, most of them have limited success and capable of revealing gross damage only.

SUMMARY OF THE INVENTION

It is against the above backgrounds that the present invention provides a non-contact method of acoustic excitation of a material in order to overcome concerns related to direct contact. In particular, the present invention provides a non-contact thermo-elastic property measurement and imaging system for quantitative nondestructive evaluation of materials. The testing and evaluation of a material by the system is based on measuring and imaging heat generation and increase of temperature due to interaction of acoustic waves with the material.

In one embodiment, a non-contact thermo-elastic imaging system for detecting defects in a structure is disclosed. The system comprises a sound source directing at least one pulse of a sound signal at a first energy level at the structure for a predetermined period of time. A thermal camera is directed towards the structure and generating thermal images of the structure when the sound source emits the at least one pulse of the sound signal. The system includes a controller coupled to the sound source and the thermal camera. The controller provides timing signals therebetween, and increases energy levels of subsequent pulses the sound pulses.

In another embodiment, a non-contact thermo-elastic imaging system for detecting defects in a structure is disclosed. The system comprises a sound source providing an ultrasonic horn. A thermal imaging camera is directed towards the structure and generating thermal images of the structure. A controller is electrically coupled to the sound source and the camera. The controller causes the sound source to transmit a series of sound pulses of increasing intensity into the structure separated by a predetermined time period at a predetermined frequency. The controller also causes the camera to generate sequential images of the structure, wherein vibrational energy from the pulses causes the defects in the structure to heat up and be visible in the images generated by the camera.

In another embodiment, a non-contact thermo-elastic method of detecting defects in a structure is disclosed. The method comprises providing a sound source having an acoustic horn having a tip placed a distance from the structure. The method includes exciting the horn with power varying from 0% to 100% in incrementing steps, and emitting a sound signal from the tip at the structure to heat the defects. The method also includes generating a sequence of thermal images of the structure before, during, and after the emission of the sound signal.

Although not limited to, the following are some noted advantages of the present invention. The concept of relating the thermo elastic parameter to heat damage and its measurements are based on thermodynamics of materials. The instrumentation provides a non-contact nondestructive technique to detect, image and quantitatively measure the heat damage in organic matrix composites.

Additional advantages and features of the present invention will become apparent from the following description and the appended claims when taken in conjunction with the accompanying drawings.

DETAILED DESCRIPTION

The following description of the embodiments of the invention directed to a non-contact nondestructive evaluation system and method thereof for testing and evaluation of a material based on measuring and imaging heat generation and increase of temperature due to interaction of acoustic waves with the material is merely exemplary in nature, and is in no way intended to limit the invention or its applications or uses.

Figure 1:
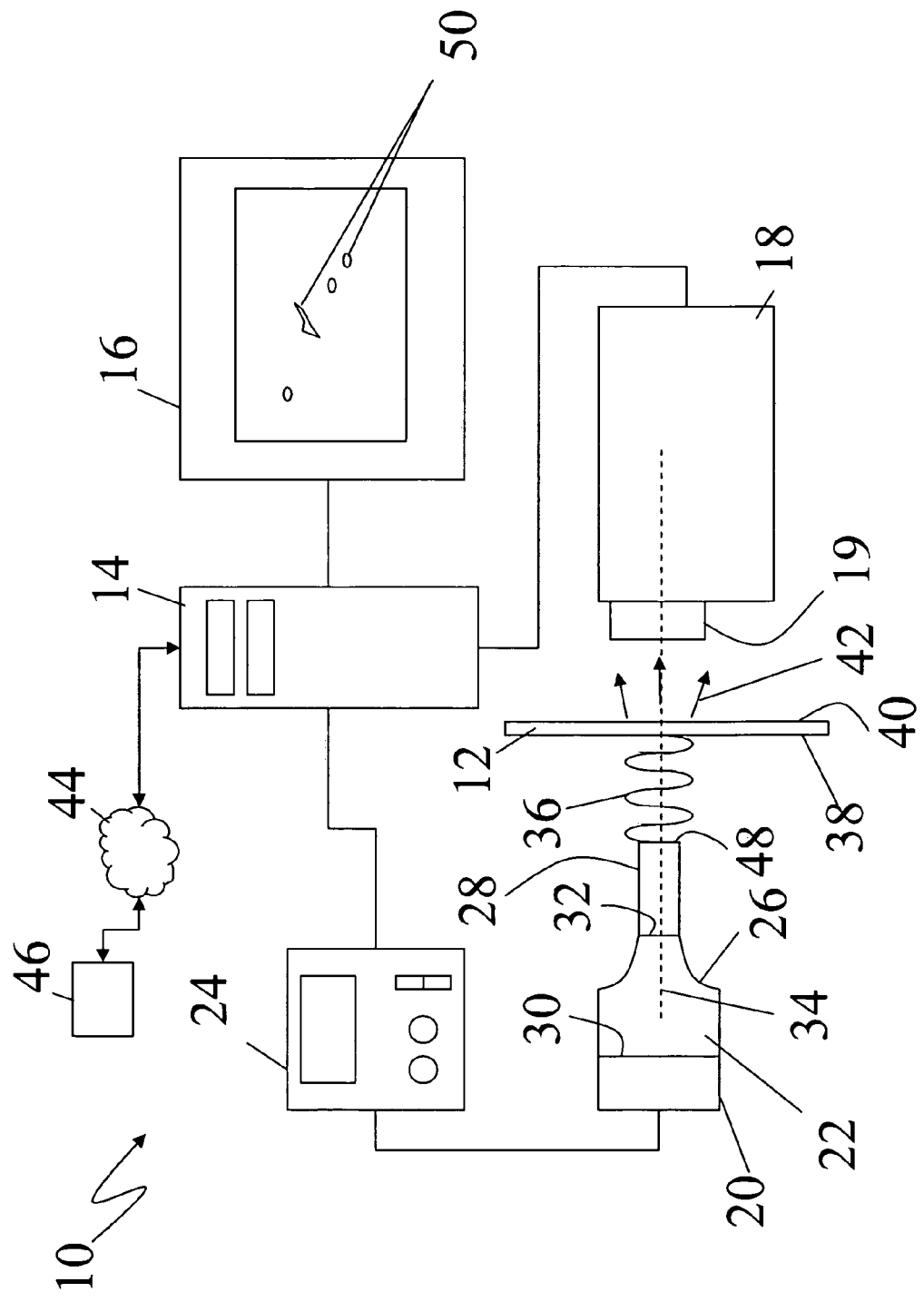
FIG. 1 is a block diagram of an imaging system according to the invention.

The basic principles of the methodology and the block diagram of a non-contact thermo-elastic property measurement and imaging system 10 are shown in FIG. 1, according to an embodiment of the present invention. The system 10 is being used to detect defects, such as cracks, corrosion, delaminations, disbonds, etc., in a specimen 12. The specimen 12 is intended to represent any structural component or material, such as an aircraft skin, turbine blades, structural welds, that may include these types of defects. It is stressed that the specimen 12 does not need to be metal, but can be other materials, organic and inorganic, such as polymers, ceramics, composites, etc.

The system 10 includes a computer 14, a computer display 16, an infrared camera 18, a vibrator 20, an ultrasonic horn 22, and a signal generator 24. The signal generator 24 generates and provides a high power radio frequency to excite the vibrator 20. The vibrator 20 may be a piezoelectric transducer or a magnetostrictive transducer, and may be coupled directly to the ultrasonic horn 22 as shown in FIG. 1 or by means of a waveguide (not illustrated). The waveguide may have any desired input: output mechanical excitation ratio, although ratios of 1:1 and 1:1.5 are typical for many applications. The vibrator 20 generates sonic or ultrasonic energy within a certain frequency band. The energy typically will have a frequency of from about 10 kHz to about 40 kHz, although other frequencies are contemplated as well. It is stressed that the frequencies and pulse time periods being described herein are by way of non-limiting examples, in that different ultrasonic frequencies, pulse times, input power, etc. will vary from system to system and specimen being tested.

In one embodiment, the ultrasonic horn 22 is of a design that resonates at a frequency of 20 kHz. The horn 22 may be provided with a tapered wall portion 26 and a tip 28, which may be cylindrical, however, other configurations are contemplated as well. In the illustrated embodiment, the tip 28 is fixed, but in other embodiments may be removable. The tapered wall portion 26 may be frustoconical, however, other configurations are contemplated as well, such as for example, elliptical, conical, bi-conic, and parabolic. In some embodiments of the present invention, the horn 22 may be composed partially or entirely of a titanium material. In one embodiment, the tapered wall portion 26 of the horn 22 is a parabolic frustum as shown by FIG. 1, and has a length of 1.625 inches (about 42 mm), which is equal to half of the resonating wavelength, and a diameter of 1.5 inch (about 38 mm). The diameter of a first end 30 of the horn 22 adjacent the vibrator 20 is 1.5 inch (about 38 mm). A second end 32 of the horn 22 adjacent the tip 28 is about 0.5 inch (about 13 mm) in diameter. The tapered wall portion 26 is approximately 1.625 inch (about 42 mm) in length, and the tip 28 is about 1.625 inch (about 42 mm) in length. The end diameter of tip 28 is 0.5 inch (about 13 mm).

When excited, the vibrator 20 causes the horn 22 to vibrate along a mechanical excitation axis 34. At a free end 48 of the tip 28 of the horn 22, the displacement about axis 34 is quite large, which further amplifies the acoustic waves generated by the vibrator 20. In particular, the horn 22 acts as an exponential mechanical amplifier, wherein in one embodiment, the displacement at the free end 48 of the tip 28 is in the range of 6 to 100 microns.

The specimen 12 is positioned a distance from the free end 48 of the tip 28 which can be adjusted. Acoustic energy symbolized by force line 36 is depicted emanating from the tip 28, propagating through the air, and impinging on a first side 38 of the specimen 12. A part of the incident acoustic energy 36 is reflected by the specimen 12 and a small portion is transmitted into the specimen. As will be explained in a later section, a part of the transmitted acoustic energy is converted into heat via thermo-elasticity, thereby producing localized increases in temperature of the specimen 12. Although the incident angle of the acoustic energy 36 from the horn 22 is shown as substantially perpendicular (about 90 degrees) to the surface of the first side 38 of the specimen, other angles of incident may be used.

In the illustrated embodiment, on a second side 40 of the sample 12, a lens 19 of the camera 18 is centered on the same axis of the horn, e.g., axis 34. The infra-red camera 18 is provided and spaced from the second side 40 of the specimen 12, and generates images of the second side 40 of the specimen 12 in association with the localized increases in temperature (excitations) of the specimen 12. The camera 18 can be spaced from the specimen 12 any suitable distance to provide images of as much of the specimen as desired in a single image. In other embodiments, the acoustic energy 36 from horn 22 and the image generated by the camera 18 can be provided at the same side of the specimen 12. The camera 18 can be any camera suitable for the purposes described herein, such as the Merlin MWIR camera available from FLIR Systems. In one embodiment, the camera 18 senses infrared emissions that are symbolized by emission lines 42 in the 3 to 5 micron wavelength range, and generates images at 60 frames per second. The camera 22 includes a focal plane array having an array of 320 by 256 pixels to generate the resolution desirable. In one embodiment, the second side 40 of the specimen 12 may be doctored to provide better contrast for infrared imaging, such as being painted black.

Figure 2B:
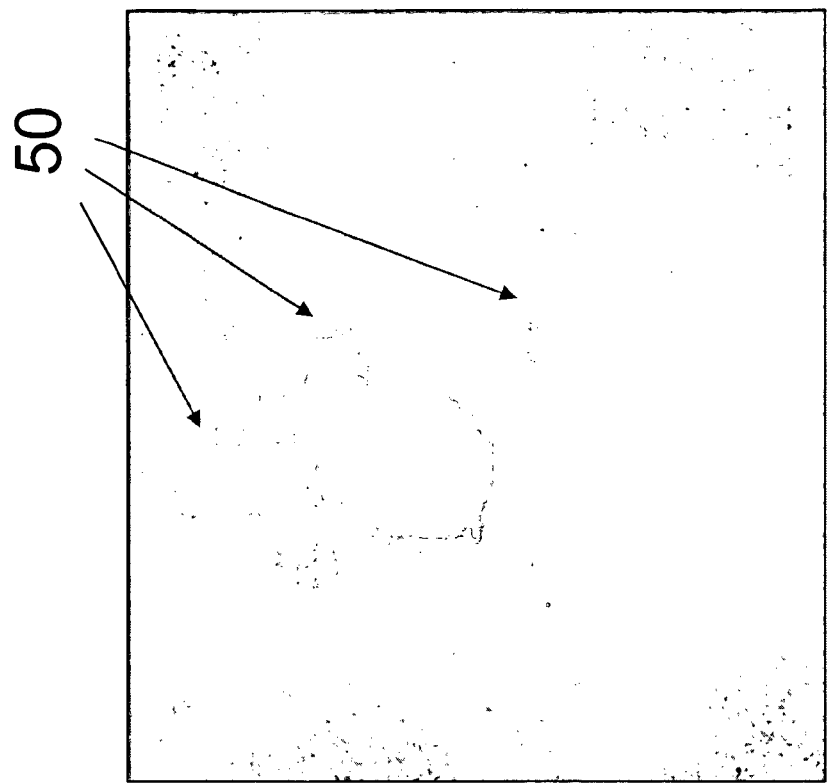
FIG. 2B is a close-up view of the image of FIG. 2A in the region outlined by line 2B-2B.
Figure 2A:
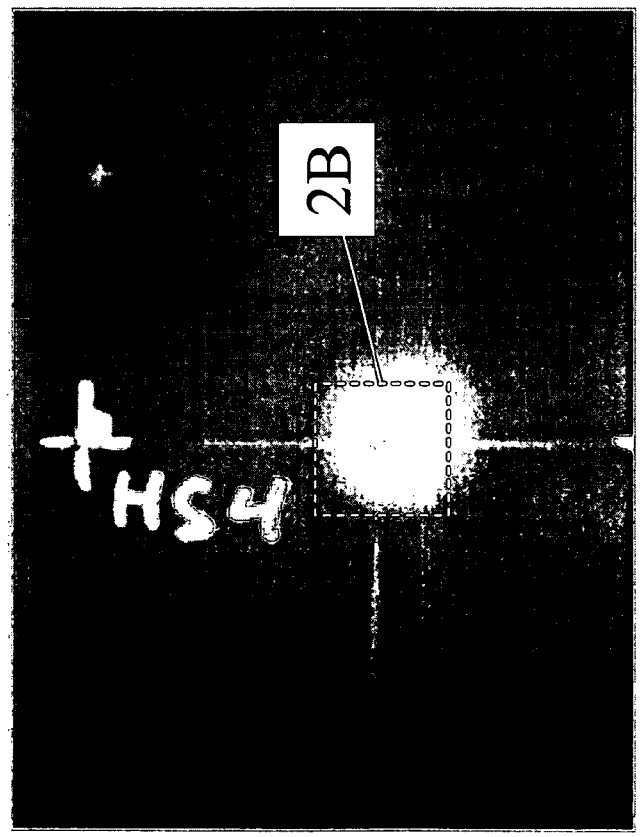
FIG. 2A is an illustration of an image of a specimen taken by the system shown in FIG. 1.

In use, the computer 14 provides timing between the vibrator 20 and the camera 18. The computer 14 can be any computer, programmable microprocessor/controller, or application specific integrated circuit (ASIC) suitable for the purposes described herein. When the detection process is initiated, the computer 14 causes the camera 18 to begin taking sequential images of the specimen 12 at a predetermined rate. Once the sequence of images begins, the computer 14 sends a signal to the signal generator 24 to send a frequency pulse of a predetermined period to the vibrator 20 such that the horn 22 generates the acoustic energy 36. After the end of the pulse, the computer 14 instructs the camera 18 to stop taking images. The images generated by the camera 18 are sent to the computer display 16 or any other monitor that displays the images taken of the specimen 12. An example of such an image is depicted by FIG. 2A. The images can be stored on the computer 14 and sent, via a network 44 connected (wired or wireless) to the computer, to an external device 46, such as a server, another computer, a database or other memory device to be viewed at another time or location if desirable.

The acoustic energy 36 applied to the specimen 12 causes faces of the defects and cracks in the specimen 12 to rub against each other and create heat. As illustrated by FIGS. 2A and 2B, this heat appears as bright spots 50 in the images generated by the camera 22, thereby showing the defects and/or cracks. The temperature generation and distribution in the material is affected by presence of cracks and defects. The acoustic energy 36 is effective to heat cracks or defects in the specimen 12, and thus it is possible to image the cracks and defects by analyzing the captured temperature images.

The change in the temperature in the material due to a longitudinal acoustic wave excitation can be expressed by Equation (1).

$$(T - T_0)/T \approx \frac{2\pi\alpha\rho V_l}{C_p}u \tag{1}$$

Where $T_0$ is the temperature of the material before excitation, T is the temperature after excitation, $\alpha$, is the thermal expansion of the material, $C_p$ is the specific heat of the material at constant pressure, $\rho$ is the density of the material, $V_l$ is the longitudinal wave velocity in the material and $\mu$ is the amplitude of the acoustic wave in the material.

In a nondestructive evaluation, the temperature change is imaged at known acoustic excitation amplitude. The change in the temperature is proportional, to the combined thermal ($\alpha$ and $C_\rho$) and elastic ($V_l$) properties of the material (Equation 1). Although, the image is purely a temperature change, the contrast variation is related to both thermal and elastic properties of the material. The image is thus useful for non-contact and nondestructive testing and evaluation of the specimen 12.

Experiments using the present invention were conducted in two stages. In the first stage, the amplitude of displacement of the acoustic horn as a function of input power to the transducer was measured using a non-contact optical probe. The first stage provided a calibration procedure for the input acoustic amplitude impinging on the specimen 12. The specimen 12 used to establish the technique was a composite panel subjected to excessive heat exposure to different amount of time at several locations on the panel. The specimen 12 had a length of 10.25 inch (260 mm), a width of 7 inch (178 mm), and a thickness of 0.085 inch (2 mm). It is to be appreciated that the thickness of the material has significant effect on temperature change. Larger the thickness, the strain produced in the material is small; hence temperature change is also small.

The specimen 12 was placed in front of the free end 48 of the acoustic horn 22 at a fixed distance of 0.015 inch (0.381 mm). It is to be appreciated that an increase in the distance between the sample and the acoustic source will reduce the acoustic amplitude. This also results in reduced temperature change.

Figure 3:
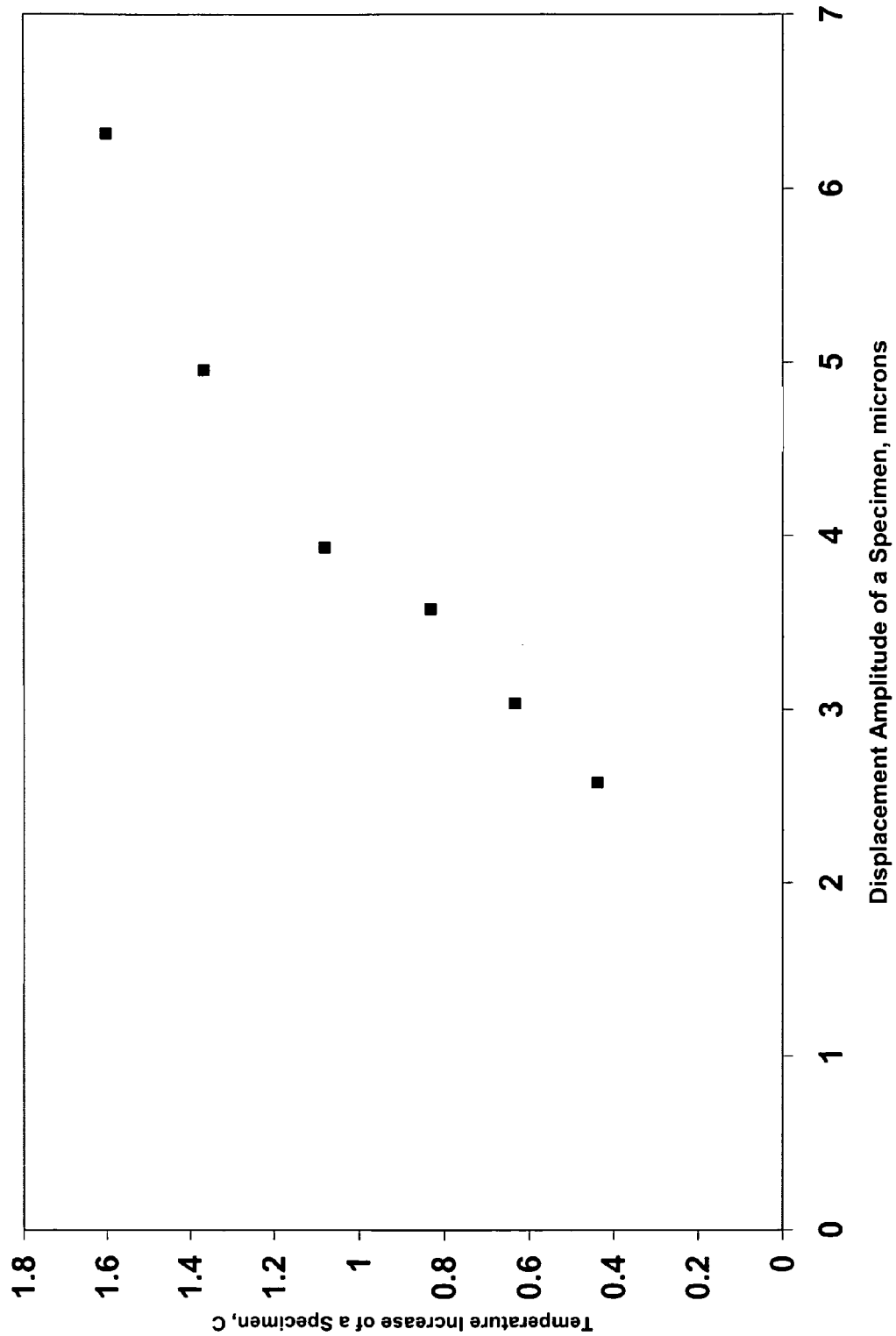
FIG. 3 is a plot of acoustic horn displacement versus input power to the transducer.

The acoustic horn 22 was excited with power varying from 0% to 100% in steps of 20% increments. This series of incremental power steps provided the acoustic energy with a varying intensity I (units of energy per unit area per unit time). A sinusoidal tone burst signal of 20 kHz from the signal generator 24 was used to excite the transducer 20 and generate a pulse of ultrasonic energy having a substantially constant amplitude at a frequency of about 20 kHz for a period of time of about 0.5 of a second. FIG. 3 is a plot of acoustic horn displacement versus input power to the transducer.

In the second stage, the camera 18 was placed on the other side of the specimen 12 at a distance of 6 inch (152 mm) and focused on a region of the specimen at which the pulse of acoustic energy 36 impinged, e.g., along axis 34. When the acoustic horn 22 was excited with each increment of power, the camera 18 captured the temperature rise in the region. The average temperature increase was measured for each excitation increment.

Figure 4:
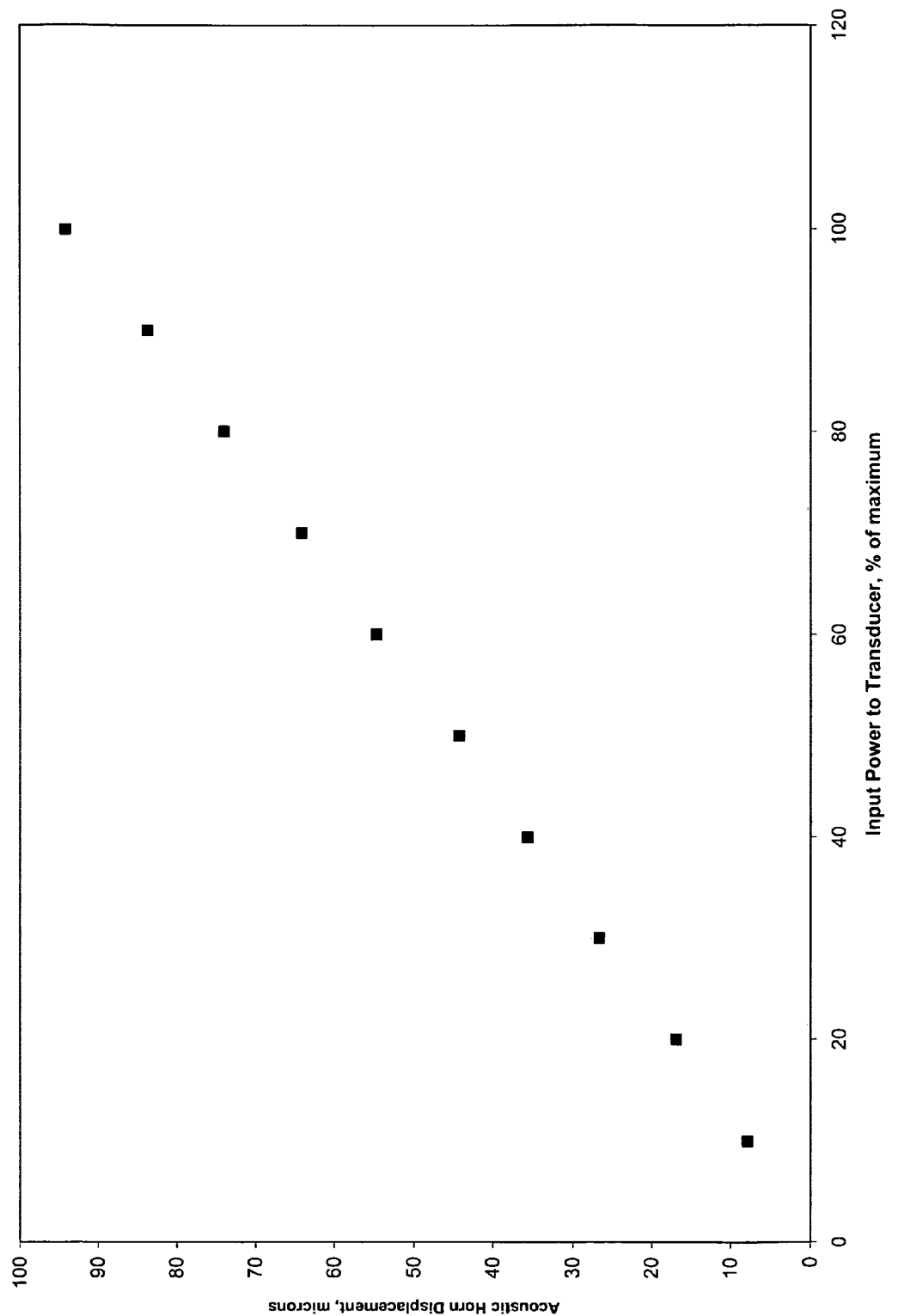
FIG. 4 is a plot of temperature increase of a specimen excited by energy from an acoustic horn versus displacement amplitude of the acoustic horn.

FIG. 4 is a plot of the localized temperature increase in the region of interest of the specimen excited by the acoustic horn 22 versus the displacement amplitude of the acoustic horn. As shown, measurements were performed on a damaged (heat affected) region and on undamaged region. In the damaged region, the temperature is observed to increase with increasing amplitude of displacement. In the undamaged region, the slope is high, while for the damaged regions it is small. The slope of the curve for different amount of time of heat exposure is also shown in FIG. 4. As indicated, as the heat-affected damage is accumulated, the rate of heat increase is found to decrease. These measurements were repeated on different specimens and similar results have been observed.

It is to be appreciated that while the non-contact NDE is an important application, the technique is useful in measurement of thermo-elastic property of the material. Generally, to measure the thermo-elastic property, the thermal and the elastic properties are measured independently and then combined. The system 10 and method described in the present invention allows direct measurement of the thermo-elastic property of the material. The system and method are very generic and applicable to variety of materials, such as metals, ceramics, polymers, and composites. The efficiency of the conversion the acoustic energy into heat depends on both thermal and elastic properties of the material. It should be noted that the temperature increase due to acoustic wave interaction in polymeric materials is at least order of magnitude larger than metals. Thus, the method according to the present invention appears to be particularly suitable to polymer and polymer composites testing.

The foregoing discussion discloses and describes merely exemplary embodiments of the present invention. One skilled in the art will readily recognize from such discussion, and from the accompanying drawings and claims, that various changes, modifications, and variations can be made therein without departing from the spirit and scope of the invention as defined in the following claims.

The invention claimed is:

1. A method of directly measuring a thermo-elastic property of a material at a first location comprising:
    providing a sound source having an ultrasonic horn having a tip positioned so that said tip does not contact the material;
    exciting said ultrasonic horn;
    emitting a series of sound signals at a single fixed frequency from said tip toward the first location of the material for a predetermined period of time, said series of sound signals having increasing energy levels, said series of sound signals separated by a predetermined time period;
    generating a sequence of thermal images of the first location before, during, and after the emission of the sound signals;
    determining the efficiency of a material to convert acoustic energy into heat from the sequence of thermal images at the first location; and
    determining a change in the efficiency of the material to convert acoustic energy into heat from the sequence of thermal images at the first location.

2. The method of claim 1, further comprising controlling said increasing energy levels, frequency of said sound signals, duration of a pulse of said sound signals, and period of generating said sequence of said thermal images.

3. The method according to claim 1, wherein said sound source comprises a signal generator which provides a high power radio frequency to excite a vibrator, said vibrator being coupled to said ultrasonic horn.

4. The method according to claim 1, wherein said sound source comprises a piezoelectric transducer coupled directly to said ultrasonic horn.

5. The method according to claim 1, wherein said sound source comprises a magnetostrictive transducer coupled directly to said ultrasonic horn.

6. The method according to claim 1, wherein said sound source comprises a signal generator which provides a high power radio frequency to excite a vibrator, said vibrator being coupled to said ultrasonic horn.

7. The method according to claim 1, wherein said sound source generates energy having a frequency in the range of from about 10 kHz to about 40 kHz.

8. The method according to claim 1, wherein said ultrasonic horn resonates at a frequency of 20 kHz.

9. The method according to claim 1, wherein said ultrasonic horn further has a tapered wall portion.

10. The method according to claim 3, wherein said ultrasonic horn further has a tapered wall portion.

11. The method according to claim 1, wherein said ultrasonic horn further has a tapered wall portion, and said tapered wall portion has a shape selected from frustoconical, parabolic frustum, elliptical, conical, bi-conic, and parabolic.

12. The method according to claim 1, wherein said ultrasonic horn has a length equal to half of a resonating wavelength.

13. The method according to claim 1, wherein said ultrasonic horn further has a tapered wall portion, said tapered wall portion is approximately 1.625 inch (about 42 mm) in length, and said tip is about 1.625 inch (about 42 mm) in length and has an end diameter of about 0.5 inch (about 13 mm).

14. The method according to claim 1, wherein said tip displaces at a free end in the range of about 6 to about 100 microns.

15. The method according to claim 1, wherein the sequence of thermal images is generated by a camera, and wherein said camera senses infrared emissions in a wavelength range of 3 to 5 microns, and generates images at 60 frames per second.

16. The method according to claim 1, wherein the sequence of thermal images is generated by a camera, and wherein said camera includes a focal plane away having an array of 320 by 256 pixels.

* * * * *